United States Patent
Turner, III (12)

(10) Patent No.: US 6,935,343 B1
(45) Date of Patent: Aug. 30, 2005

(54) INTERNAL ALLOTROPY IMPLEMENT SEXUAL AID UTENSIL ADVANCED PLUS

(76) Inventor: Jacob Turner, III, 11115 Sherman Way, Apt. 203, Sun Valley, CA (US) 91352

( * ) Notice: Subject to any disclaimer, the term of this patent is extended or adjusted under 35 U.S.C. 154(b) by 0 days.

(21) Appl. No.: 10/199,890

(22) Filed: Jul. 19, 2002

(51) Int. Cl.⁷ .................................................. A61F 5/37
(52) U.S. Cl. ...................................... 128/883; 128/884
(58) Field of Search ................................ 128/830, 840, 128/883, 884

(56) References Cited

U.S. PATENT DOCUMENTS

| | | | | |
|---|---|---|---|---|
| 4,167,183 A | * | 9/1979 | Barlow | 128/884 |
| 4,237,876 A | * | 12/1980 | Rumph | 128/884 |
| 5,769,090 A | * | 6/1998 | Brown | 128/883 |
| 6,250,304 B1 | * | 6/2001 | Turner | 128/883 |

* cited by examiner

*Primary Examiner*—Michael A. Brown
(74) *Attorney, Agent, or Firm*—Jacob B Turner, III

(57) ABSTRACT

The invention is made of a soft and firm two types of FDA medically approved polymer thermoplastics containing within its structure different hardness and shapes of a hollow resilient tip, elongated one piece member being a sharp projectile. The resilient tip can be filled with a spermicide. The device is inserted into the vagina of the woman wearing it in the same way as a tampon lengthwise and pushing it into the vaginal cavity. Upon placement in the vagina, the invention blocks the entrance to the vagina, and exposes a resilient hollow tip covering a sharp projectile, which once compressed will inflict a sharp non-lethal pain to head of the penis attempting to penetrate the vagina. The invention is stablized inside the vagina. A woman can pinch grip the resilient tip to remove the device. The device is disposable. A Physican should be consulted in regards for proper maintenance of the device. It can be made in different sizes to accommodate the various different female bodies. It can be worn by woman of all ages.

8 Claims, 4 Drawing Sheets

"SHORT 50"

"LONG 7"

INTERNAL ALLOTROPY IMPLEMENT SEXUAL AID UTENSIL ADVANCED PLUS

BRIEF SUMMARY

This type of invention is one that causes a non-lethal severe sharp pain to the head of the male penis and creates a blockage device inserted into the female vagina. The invention is made to prevent unwanted penal penetration, and to give a non-lethal pain if forced vagina penetration is attempted. It is an intra-vaginal anti-rape invention which is made of two medically approved FDA polymer thermoplastic material. It's structure consist of a two part interlocking internal personal prevention device worn inside the female vagina. A resilient hollow tip, which covers a one piece sharp projectile, and holds a contraceptive solution, which is attached to a circular member which has the aperture therein with a string to remove or insert the device which secures the invention together and fill the vaginal cavity. The elongated implant can be substituted for a tampon depending upon the female using the invention. This invention is disposable. The purpose of the invention is to create a vaginal blocker internally with a sharp pointed projectile covered by a resilient hollow tip inside a cavity which will inflict a sharp abrupt severe pain to the head of a male's penis if forced penetration is attempted. The invention is made to be worn by women of all ages. Size adjustments can be made according to each individual woman wearing the invention. Men considering rape, after this invention becomes known, will hopefully not attempt it, with the dread that any women could be wearing this invention.

DETAILED DESCRIPTION

Figure 1:
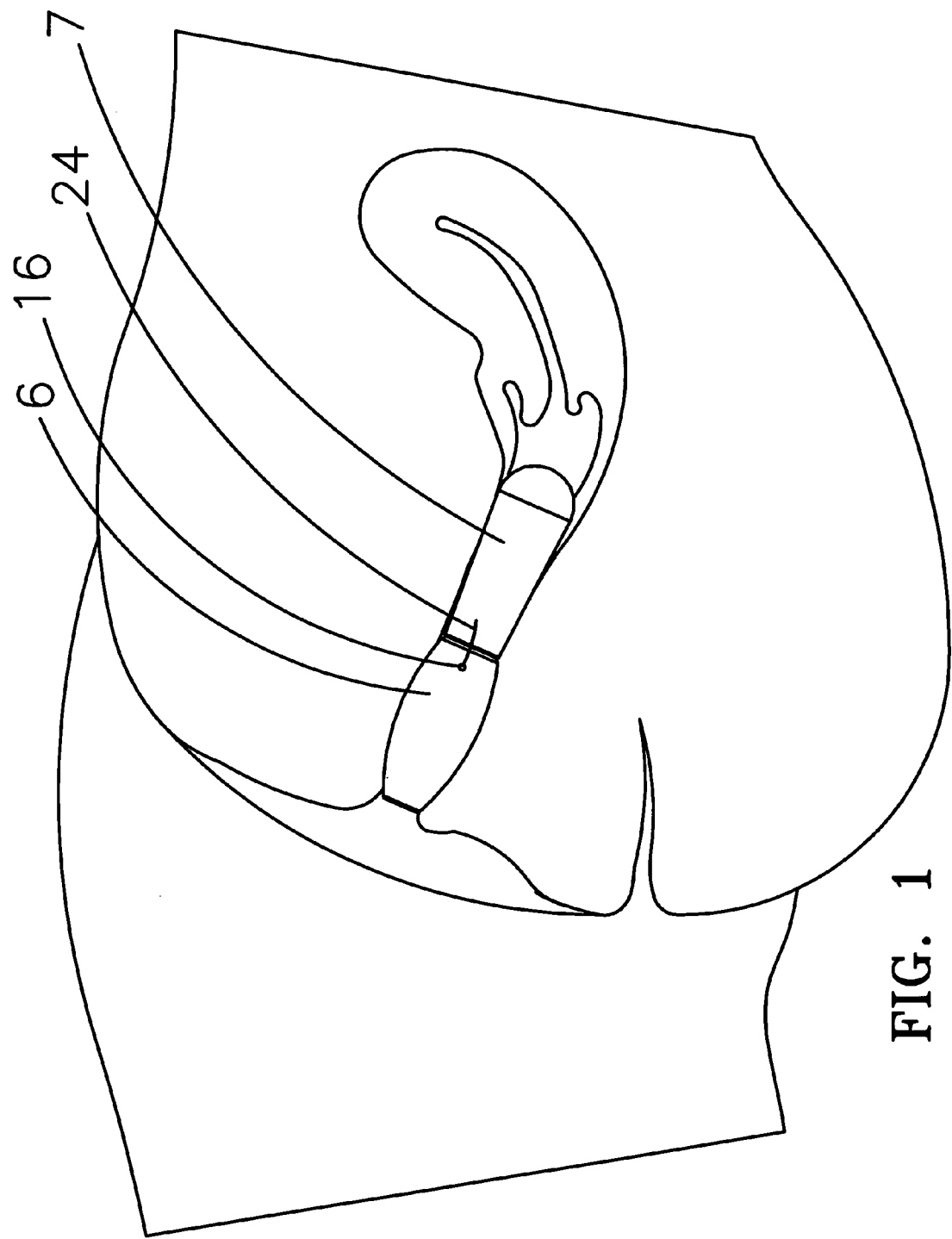
FIG. 1, shows the internal allotropy implement sexual aid utensil advanced PLUS device is shown. The long member 7, is attached to the hollow resilient tip 6, an aperture 16, a string 24, attached in the aperture to remove or insert the device.
Figure 3:
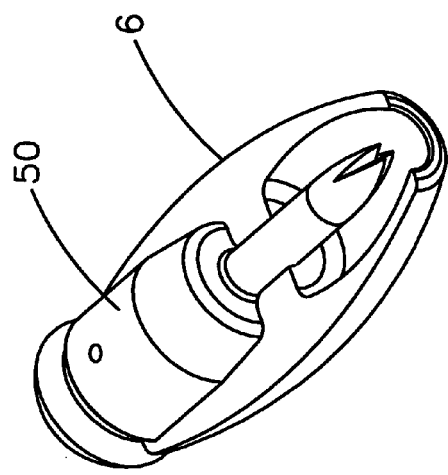
FIG. 3, shows crossview of short member 50 is shown. The short member includes hollow resilient tip 6.
Figure 2:
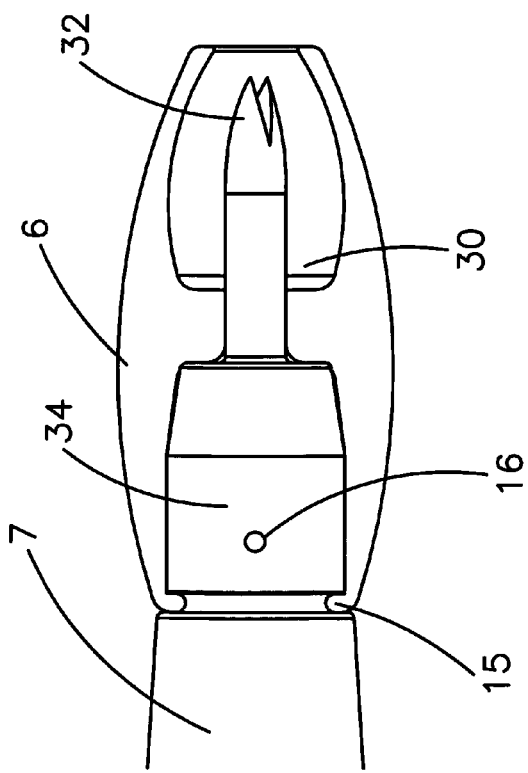
FIG. 2, shows a sideview of the device is shown. The long member 7, is attached to the hollow resilient tip 6, by a ribbed member 15, a circular member 34, has the aperture 16 therein. The tubular hollow resilient tip 6, has therein a sharp projectile 32, inside a hollow cavity 30.
Figure 5:
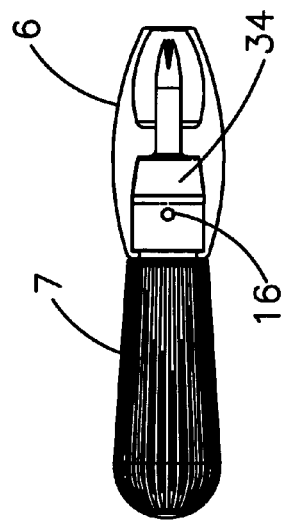
FIG. 5, shows an internal allotropy implement sexual aid utensil advanced PLUS device sideview is shown attached with conventional tampon 55. Conventional tampon is attached to cover cap 22, which is attached to tubular member 34.
Figure 4:
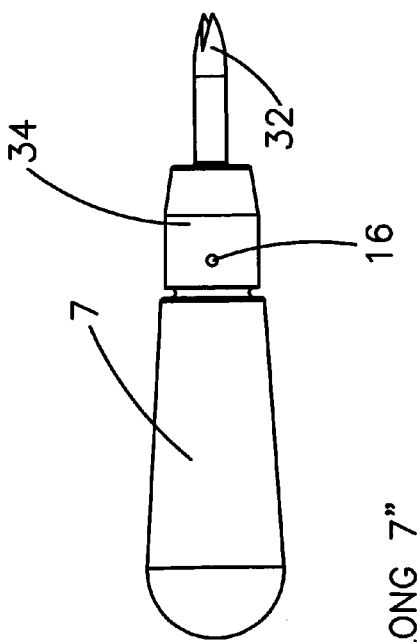
FIG. 4, shows long circular member 7, is attached to the one piece circular member 34, has the aperture 16, therein sharp projectile 32.
Figure 6:
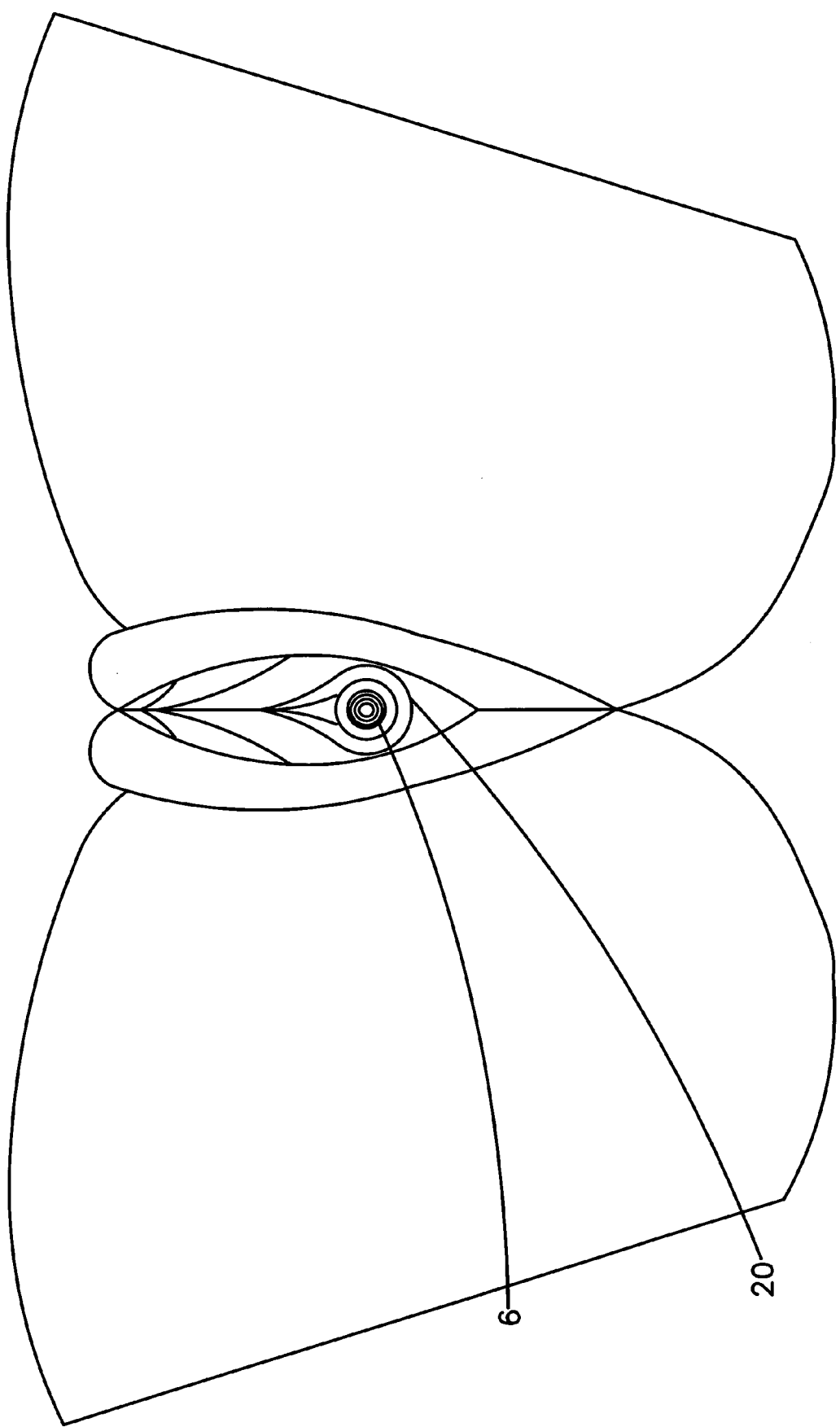
FIG. 6, shows frontal view of vaginal entrance with internal allotropy implement sexual aid utensil advance PLUS 6, inside vaginal cavity 20.
Figure 8:
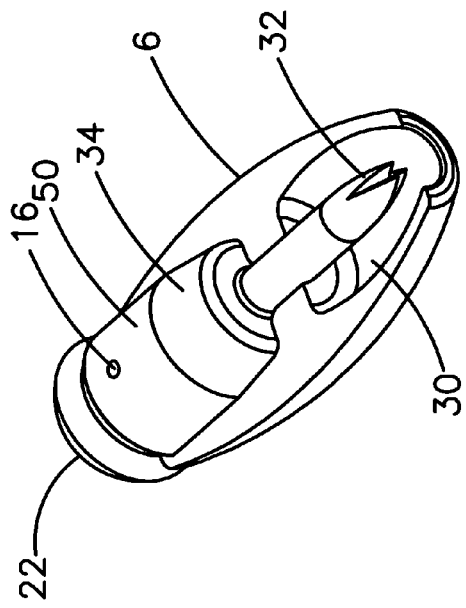
FIG. 8, shows crossview of short member 50, is shown. The short member includes hollow resilient tip 6, the hollow cavity 30, the short member 50, the aperture 16, a circular member 34, sharp projectile 32, and a cover cap 22.
Figure 7:
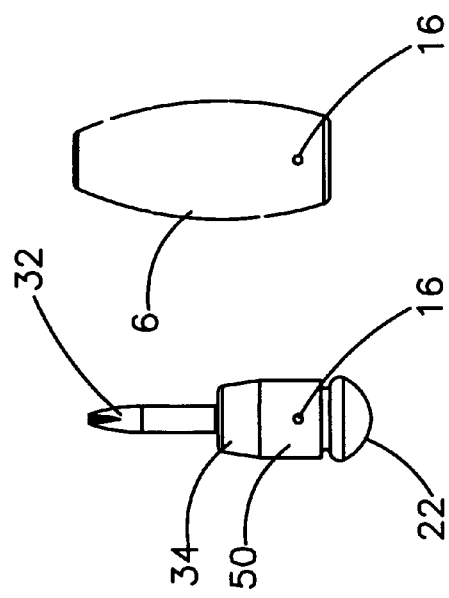
FIG. 7, shows the one piece tubular member 50, the circular member 34, an aperture 16, sharp projectile 32, the cover cap 22, and the hollow resilient tip 6.
Figure 11:
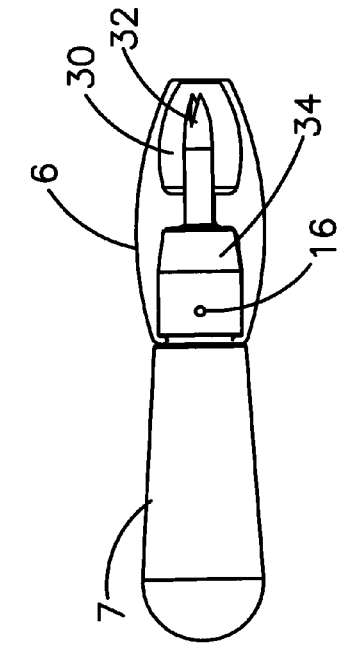
FIG. 11, shows a sideview of the long one piece tubular member 7, attached to circular member 34. The aperture 16, sharp projectile 32, hollow resilient tip 6, and a hollow cavity 30.
Figure 10:
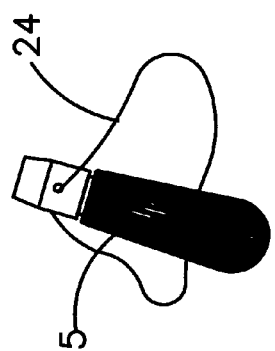
FIG. 10, shows a conventional tampon 55, attached to the string 24.
Figure 9:
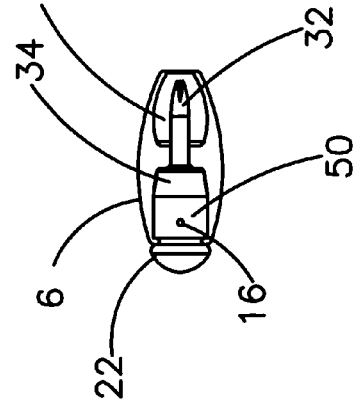
FIG. 9, shows sideview of short one piece tubular member 50, the circular member 34, an aperture 16, the sharp projectile 32, the cover cap 22, includes the hollow resilient tip 6, the hollow cavity 30.

The internal allotropy implement sexual aid utensil advanced PLUS includes a two part interlocking internal personal prevention device worn in the female vagina. In FIG. 1, the internal allotropy implement sexual aid utensil advanced PLUS device is shown. The device includes a tubular member being a hollow resilient tip 6, an aperture 16, a string 24, attached in the aperture to remove or insert the device. The long member 7, is attached to the hollow resilient tip 6. In FIG. 2, a side view of the device is shown. The long member 7, is attached to the hollow resilient tip 6, by a ribbed member 15. A circular member 34, has the aperture 16 therein. The tubular hollow resilient tip 6, has therein a sharp projectile 32, inside a hollow cavity 30. In FIG. 3, crossview of short member 50 is shown. The short member includes hollow resilient tip 6. In FIG. 4, long circular member 7, is attached to the one piece circular member 34. In FIG. 5, an internal allotropy implement sexual aid utensil advanced PLUS device sideview is shown attached with a conventional tampon 55. Conventional tampon is attached to cover cap 22, which is attached to tubular member 34. In FIG. 6, frontal view of vaginal entrance with internal allotropy implement sexual aid advanced PLUS 6, inside vaginal cavity 20. FIG. 7, shows the one piece short member 50, the circular member 34, an aperture 16, sharp projectile 32, the cover cap 22, and the hollow resilient tip 6. In FIG. 8, crossview of short member 50, is shown. The short member 50, includes hollow resilient tip 6, the hollow cavity 30, the aperture 16, a circular member 34, sharp projectile 32, and cover cap 22. FIG. 9, shows sideview of short one piece tubular member 50, the circular member 34, an aperture 16, the sharp projectile 32, the cover cap 22, and the hollow resilient tip 6. In FIG. 10, a conventional tampon 55, is attached to the string 24. FIG. 11, shows a sideview of the long one piece tubular member 7, attached to circular member 34. The aperture 16, sharp projectile 32, hollow resilient tip 6, and a hollow cavity 30. These parts are made with two medically approved polymers, and this device is disposable. The resilient tip 6, is designed to contain a spermicide or a lubricant.

What I claim as my invention is:

1. An anti-rape device comprising a hollow cap member, said hollow cap member extending inside of a resilient tubular member, a sharp projectile extending through a cavity in said hollow cap member and a cavity in said resilient tubular member, a cap cover attached to an end of said resilient tubular member by a connecting means, an elongated means for absorbing attached to said cap cover and a means for removing said anti-rape device is attached to said absorbing means.

2. The anti-rape device of claim 1, further comprising a long cylindrically tapered member that is attached to said resilient tubular member by said connecting means.

3. The anti-rape device of claim 2, wherein said connecting means is a rib.

4. The anti-rape device of claim 1, further comprising an aperture in said resilient tubular member, wherein said means for removing passes through said aperture.

5. The anti-rape device of claim 1, further comprising a contraceptive solution inside of said resilient hollow tubular member.

6. The anti-rape device of claim 1, wherein said cap cover, said resilient hollow tubular member and said hollow cap member form a short anti-rape device.

7. The anti-rape device of claim 1, wherein said long cylindrically tapered member, said resilient hollow tubular member, said hollow cap member form a long anti-rape device.

8. The anti-rape device of claim 1, further comprising a circular member attaching said sharp projectile to said resilient hollow member.

\* \* \* \* \*